US009687211B2

(12) United States Patent
Okuno

(10) Patent No.: US 9,687,211 B2
(45) Date of Patent: Jun. 27, 2017

(54) ULTRASOUND ENDOSCOPE SYSTEM AND COMMUNICATION METHOD OF THE ULTRASOUND ENDOSCOPE SYSTEM

(71) Applicant: OLYMPUS CORPORATION, Tokyo (JP)

(72) Inventor: Yoshiyuki Okuno, Fussa (JP)

(73) Assignee: OLYMPUS CORPORATION, Tokyo (JP)

( * ) Notice: Subject to any disclaimer, the term of this patent is extended or adjusted under 35 U.S.C. 154(b) by 15 days.

(21) Appl. No.: 14/967,781

(22) Filed: Dec. 14, 2015

(65) Prior Publication Data

US 2016/0095578 A1     Apr. 7, 2016

Related U.S. Application Data

(63) Continuation of application No. PCT/JP2014/075599, filed on Sep. 26, 2014.

(30) Foreign Application Priority Data

Oct. 1, 2013  (JP) .................................. 2013-206593

(51) Int. Cl.
*A61B 8/00*      (2006.01)
*A61B 8/12*      (2006.01)
(Continued)

(52) U.S. Cl.
CPC ........ *A61B 8/4416* (2013.01); *A61B 1/00009* (2013.01); *A61B 1/00055* (2013.01);
(Continued)

(58) Field of Classification Search
None
See application file for complete search history.

(56) References Cited

U.S. PATENT DOCUMENTS

2006/0276687 A1   12/2006   Sato
2008/0249361 A1*  10/2008   Okuno ............... A61B 1/00039
                                                        600/118
2009/0029647 A1*   1/2009   Wei .......................... G06F 3/147
                                                        455/41.3

FOREIGN PATENT DOCUMENTS

EP       1728463 A1   12/2006
EP       1977695 A1   10/2008
(Continued)

OTHER PUBLICATIONS

International Search Report dated Oct. 28, 2014 issued in PCT/JP2014/075599.
(Continued)

*Primary Examiner* — Long V Le
*Assistant Examiner* — Marjan Saboktakin
(74) *Attorney, Agent, or Firm* — Scully, Scott, Murphy & Presser, P.C.

(57) ABSTRACT

An ultrasound endoscope system includes: an ultrasound endoscope that wirelessly transmits and receives endoscope state information; a video processor including a first read-out section that reads out the endoscope state information of the ultrasound endoscope; an ultrasound observation apparatus including a second read-out section that reads out endoscope state information obtained by a communication section for observation apparatus; and a control section that compares the endoscope state information obtained by the first read-out section in the video processor and the endoscope state information obtained by the second read-out section in the ultrasound observation apparatus, and causes sharing of information related to a subject to be started between the video processor and the ultrasound observation apparatus only when the endoscope state information obtained by the first read-out section and the endoscope state
(Continued)

information obtained by the second read-out section match with each other.

7 Claims, 5 Drawing Sheets

(51) Int. Cl.
*A61B 1/00* (2006.01)
*A61B 1/04* (2006.01)

(52) U.S. Cl.
CPC ................ *A61B 1/04* (2013.01); *A61B 8/12* (2013.01); *A61B 8/4472* (2013.01); *A61B 8/463* (2013.01); *A61B 8/565* (2013.01); *A61B 8/445* (2013.01); *A61B 8/4438* (2013.01); *A61B 8/54* (2013.01)

(56) References Cited

FOREIGN PATENT DOCUMENTS

| | | | |
|---|---|---|---|
| JP | 2006-334169 | A | 12/2006 |
| JP | 2007-275087 | A | 10/2007 |
| JP | 2008-253525 | A | 10/2008 |
| JP | 4727302 | B2 | 7/2011 |
| JP | 4908897 | B2 | 4/2012 |
| JP | 5064868 | B2 | 10/2012 |

OTHER PUBLICATIONS

Japanese Office Action dated Jun. 3, 2015 issued in JP 2015-516364.

\* cited by examiner

ULTRASOUND ENDOSCOPE SYSTEM AND COMMUNICATION METHOD OF THE ULTRASOUND ENDOSCOPE SYSTEM

CROSS REFERENCE TO RELATED APPLICATION

This application is a continuation application of PCT/JP2014/075599 filed on Sep. 26, 2014 and claims benefit of Japanese Application No. 2013-206593 filed in Japan on Oct. 1, 2013, the entire contents of which are incorporated herein by this reference.

BACKGROUND OF THE INVENTION

1. Field of the Invention

The present invention relates to an ultrasound endoscope system, connection of which is simplified, and a communication system of the ultrasound endoscope system.

2. Description of the Related Art

An ultrasound endoscope is capable of outputting an endoscopic image (optical image) obtained by an image pickup device and an ultrasound image obtained by an ultrasound transducer. Output from the ultrasound endoscope is fed to a video processor that processes an optical image, thereby enabling an endoscopic image to be displayed on a monitor. Further, output from the ultrasound endoscope is fed to an ultrasound observation apparatus that processes an ultrasound image, thereby enabling an ultrasound image to be displayed on the monitor. Furthermore, the ultrasound endoscope is connected to both of the video processor and the ultrasound observation apparatus, thereby enabling patient information to be commoditized in the video processor and the ultrasound observation apparatus. Therefore, the examination status for each patient with the use of the endoscopic image and the ultrasound image can be collectively managed. As a result, decision from multifaceted viewpoint is possible in determining a diagnosis policy, which is useful at the time of making diagnosis.

That is, the video processor and the ultrasound observation apparatus, both of which are connected with the ultrasound endoscope, share setting information and the images each other, thereby capable of managing the examination status in an integrated fashion. For the purpose of such information sharing, the ultrasound endoscope and the respective apparatuses are connected to each other with cables and the like.

However, the ultrasound endoscope is required to be cleaned after having been used for diagnosis, and at the time of cleaning, the cables used for connecting the ultrasound endoscope with the video processor and the ultrasound observation apparatus have to be removed. Thus, before and after the cleaning processing, the cables connecting the ultrasound endoscope with the video processor and the ultrasound observation apparatus have to be attached to and detached from the ultrasound endoscope, which requires a troublesome operation for an operator.

Note that Japanese Patent No. 4908897 (hereinafter, referred to as Document 1) proposes a technique of performing wireless communication with an ultrasound probe in an ultrasound observation apparatus for body surface. In the proposal in Document 1, the section that communicates ultrasound signals is configured to be wireless, to eliminate attaching and detaching operations of the cable that connects the section and the ultrasound observation apparatus, which reduces efforts.

SUMMARY OF THE INVENTION

An ultrasound endoscope system according to the present invention is an ultrasound endoscope system including: an ultrasound endoscope that is capable of performing optical observation; a video processor for optical observation which is connected to the ultrasound endoscope through a wire; and an ultrasound observation apparatus for ultrasound observation, the ultrasound endoscope including: an image pickup section that obtains an optical image from a subject; an ultrasound transducer that transmits and receives ultrasound to and from the subject; and a communication section for endoscope that wirelessly transmits and receives an ultrasound signal obtained from the ultrasound received by the ultrasound transducer and endoscope state information as endoscope-specific information, the video processor including: an image output section that performs image signal processing on the optical image obtained by the image pickup section; and a first read-out section that reads out the endoscope state information of the ultrasound endoscope, and the ultrasound observation apparatus including: a transmission/reception section that is capable of transmitting and receiving the ultrasound signal; a communication section for observation apparatus that wirelessly communicates with the communication section for endoscope, and transmits and receives the ultrasound signal and the endoscope state information; an ultrasound image processing section that generates an ultrasound image based on the ultrasound signal obtained by the communication section for observation apparatus; and a second read-out section that reads out the endoscope state information obtained by the communication section for ultrasound observation apparatus, the ultrasound endoscope system further including, a control section that compares the endoscope state information obtained by the first read-out section in the video processor and the endoscope state information obtained by the second read-out section in the ultrasound observation apparatus, and causes sharing of information related to the subject to be started between the video processor and the ultrasound observation apparatus only when the endoscope state information obtained by the first read-out section and the endoscope state information obtained by the second read-out section match with each other.

A communication method of an ultrasound endoscope system according to the present invention is a communication method of an ultrasound endoscope system including an ultrasound endoscope that is capable of performing optical observation; a video processor for optical observation which is connected to the ultrasound endoscope through a wire; and an ultrasound observation apparatus for ultrasound observation, the method including: a step in which a first read-out section in the video processor connected to the ultrasound endoscope through the wire reads out endoscope state information of the ultrasound endoscope; a step in which a communication section for observation apparatus in the ultrasound observation apparatus wirelessly communicates with a communication section for endoscope in the ultrasound endoscope and receives the endoscope state information; and a step in which a control section cross-checks the endoscope state information received by the video processor and the endoscope state information received by the communication section for observation apparatus against each other, to perform determination of matching of the pieces of endoscope state information, and performs control for causing sharing of information related to a subject to be started between the video processor and the ultrasound observation apparatus when determining that the pieces of endoscope state information match with each other.

DETAILED DESCRIPTION OF THE PREFERRED EMBODIMENTS

Hereinafter, embodiments of the present invention will be described with reference to drawings.

First Embodiment

Figure 1:
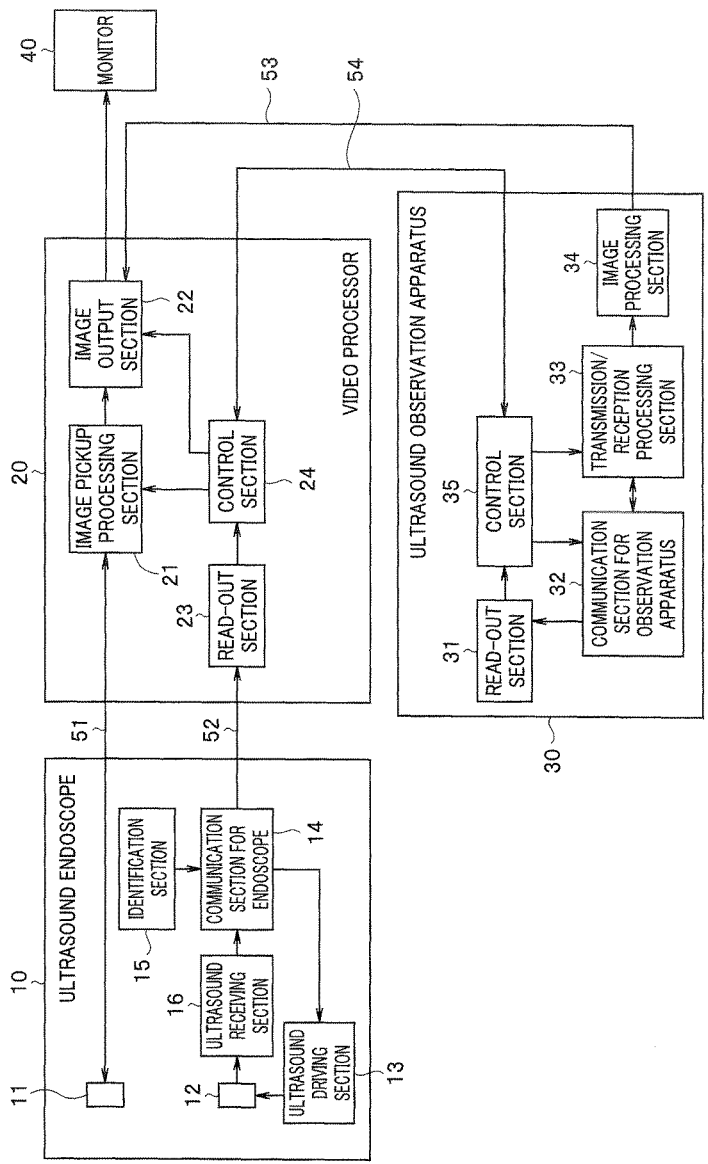
FIG. 1 is a block diagram for showing an ultrasound endoscope system according to a first embodiment of the present invention.

FIG. 1 is a block diagram showing an ultrasound endoscope system according to the first embodiment of the present invention. The present embodiment enables the ultrasound endoscope and the ultrasound observation apparatus to be connected to each other by wireless communication.

In FIG. 1, an ultrasound endoscope 10 and a video processor 20 can be connected to each other with a cable 51. The cable 51 includes, on each of the both ends thereof, a connector not shown, and the connectors are connected respectively with the ultrasound endoscope 10 and the video processor 20, to allow the ultrasound endoscope 10 and the video processor 20 to be connected to each other in detachable manner through the cable 51. On the other hand, the ultrasound endoscope 10 and the ultrasound observation apparatus 30 are connected to each other by wireless communication as described later.

The ultrasound endoscope 10 includes an image pickup section 11 that obtains optical images. The image pickup section 11 is constituted of a CCD, a CMOS sensor, or the like, and configured to photoelectrically convert an optical image from an object and output the photoelectrically converted optical image as an endoscopic image. The endoscopic image outputted from the image pickup section 11 is fed to an image pickup processing section 21 of the video processor 20 through the cable 51.

The image pickup processing section 21 of the video processor 20 is controlled by a control section 24, to drive and control the image pickup section 11 of the ultrasound endoscope 10 and output the endoscopic image from the image pickup section 11 to an image output section 22. The image output section 22 is controlled by the control section 24, to perform a predetermined image signal processing on the endoscopic image and output the endoscopic image subjected to the image signal processing to the monitor 40.

In addition, the image output section 22 receives the ultrasound image from an image processing section 34 in the ultrasound observation apparatus 30 to be described later, through a communication line 53. The image output section 22 is capable of outputting the endoscopic image and the ultrasound image independently to the monitor 40, and also capable of combining the endoscopic image and the ultrasound image, to output the combined image to the monitor 40. The monitor 40 is configured to display the inputted image on a display screen, not shown.

The ultrasound endoscope 10 includes a transducer 12 for transmitting and receiving ultrasound, an ultrasound driving section 13, and an ultrasound receiving section 16. The ultrasound driving section 13 drives the transducer 12 based on control information fed from a communication section for endoscope 14. The transducer 12 is driven by the ultrasound driving section 13, to repeatedly transmit ultrasound pulses into a living body and receive echoes of the ultrasound pulses reflected from inside of the living body. The ultrasound receiving section 16 processes a received signal received by the transducer 12, to transmit the processed signal to the communication section for endoscope 14.

In addition, the ultrasound endoscope 10 is provided with an identification section 15 which stores endoscope-specific information. The identification section 15 is configured to output the endoscope-specific information to the communication section for endoscope 14. The communication section for endoscope 14 is configured to be able to read out the endoscope-specific information stored in the identification section 15 and output the read-out information to a read-out section 23 in the video processor 20 through a cable 52. Note that, the cable 52 is capable of detachably connecting the ultrasound endoscope 10 and the video processor 20 to each other through the use of a connector, not shown. In addition, the cable 51 and the cable 52 may be a common cable. The endoscope-specific information may be transmitted via a connector, not shown, of the cable 52, instead of the cable 51.

The read-out section 23 of the video processor 20 reads out the endoscope-specific information transmitted from the communication section for endoscope 14 of the ultrasound endoscope 10, to output the read-out information to the control section 24. The control section 24 controls the respective sections in the video processor 20, and communicates with a control section 35 of the ultrasound observation apparatus 30 to be described later, through a communication line 54. That is, the video processor 20 and the ultrasound observation apparatus 30 communicate with each other by wire communication through the communication lines 53, 54. When the ultrasound endoscope 10 is cleaned, the video processor 20 and the ultrasound observation apparatus 30 may remain connected to each other through the communication lines 53, 54.

In the present embodiment, the ultrasound observation apparatus 30 is provided with a communication section for observation apparatus 32. The communication section for endoscope 14 of the ultrasound endoscope 10 and the communication section for observation apparatus 32 have a wireless communication function, and are capable of communicating wirelessly with each other.

The communication section for endoscope 14 receives information related to ultrasound driving from the ultrasound observation apparatus 30, and transmits the received signal, which has been received by the transducer 12 and then fed from the ultrasound receiving section 16, to the ultrasound observation apparatus 30. Furthermore, the communication section for endoscope 14 reads out the endoscope-specific information stored in the identification section 15, and transmits the read-out information to the ultrasound observation apparatus 30 by wireless communication.

A transmission/reception processing section 33 of the ultrasound observation apparatus 30 is controlled by the control section 35, to perform transmission/reception processing for the ultrasound observation apparatus 30. The communication section for observation apparatus 32 is controlled by the transmission/reception processing section 33, to receive an ultrasound image and transmit the information for ultrasound driving, which has been fed from the control section 35, to the ultrasound endoscope 10. The communication section for observation apparatus 32 outputs the received ultrasound image to the image processing section 34 through the transmission/reception processing section 33.

The image processing section 34 performs predetermined image signal processing on the inputted ultrasound image. The transmission/reception processing section 33 is controlled by the control section 35, to enable the ultrasound image subjected to the image processing in the image processing section 34 to be transmitted to the image output section 22 of the video processor 20 through the communication line 53.

In addition, the communication section for observation apparatus 32 is controlled by the transmission/reception processing section 33, to receive endoscope-specific information. A read-out section 31 reads out the endoscope-specific information, which has been received by the communication section for observation apparatus 32, to output the read-out information to the control section 35.

The control section 35 determines whether or not the communication is appropriately established between the ultrasound observation apparatus 30 and the ultrasound endoscope 10 by using the endoscope-specific information which has been read out by the read-out section 31. That is, the control section 35 of the ultrasound observation apparatus 30 and the control section 24 of the video processor 20 communicate with each other through the communication line 54, to cross-check the endoscope-specific information read out from the read-out section 31 and the endoscope-specific information read out from the read-out section 23 against each other. Based on the cross-check, the control sections 24 and 35 determine whether the wire connection and the wireless connection are normally established, that is, determine whether communication between the ultrasound endoscope 10 connected to the video processor 20 through the wire and the ultrasound observation apparatus 30 is established wirelessly.

When determining that the wireless communication has been established between the ultrasound endoscope 10 connected to the video processor 20 through the wire and the ultrasound observation apparatus 30, the control section 35 shares information with the control section 24 and controls the transmission/reception processing section 33 to cause the transmission/reception processing section 33 to transmit the ultrasound image to the video processor 20.

Figure 2:
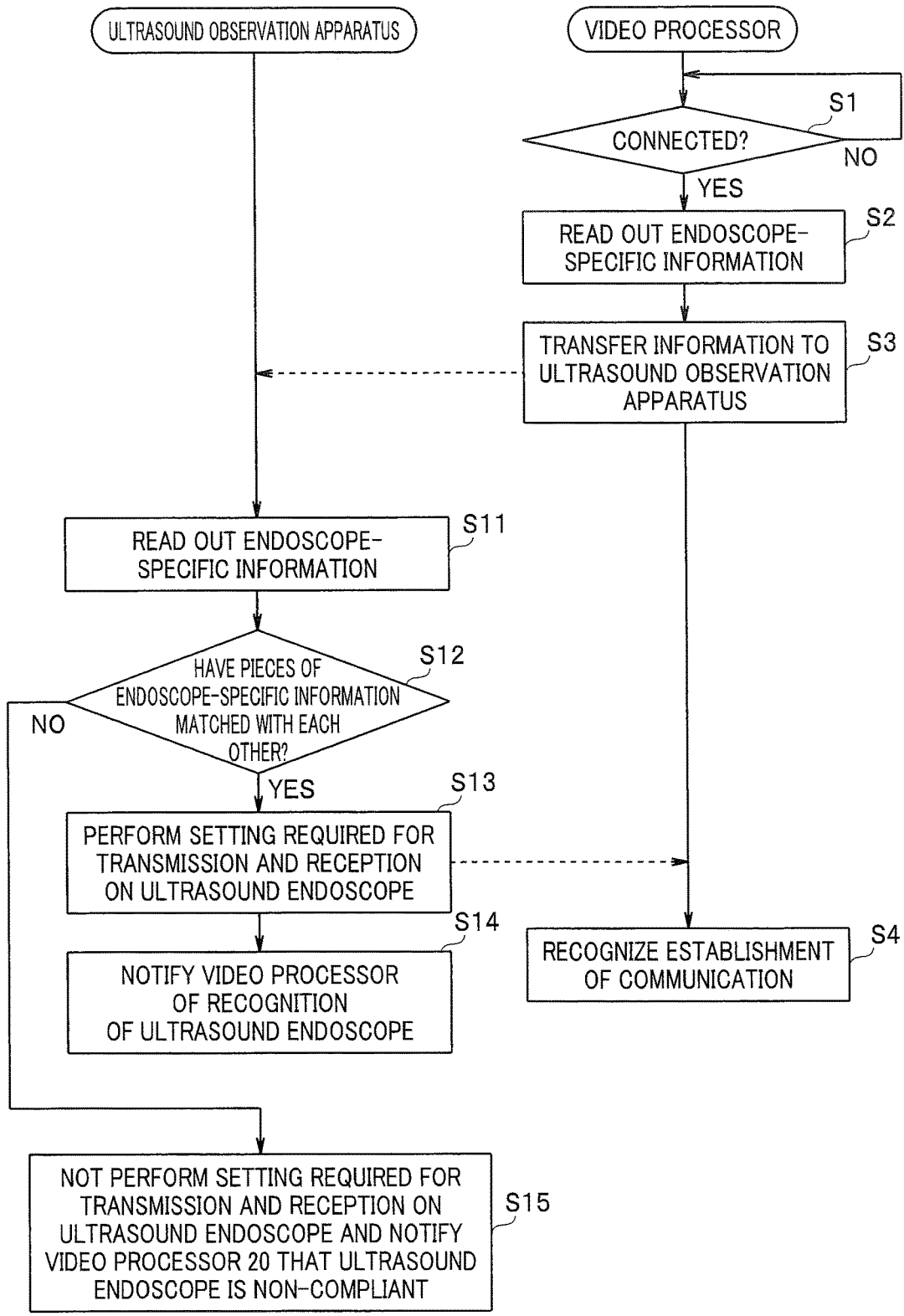
FIG. 2 is a flowchart for describing an operation in the first embodiment.

Next, the operation in the present embodiment thus configured will be described with reference to the flowchart in FIG. 2. The left side in FIG. 2 shows the operation of the ultrasound observation apparatus 30, the right side in FIG. 2 shows the operation of the video processor 20, and each of the dashed-line arrows shows communication.

The video processor 20 determines whether or not the ultrasound endoscope 10 is connected in step S1. When the ultrasound endoscope 10 is connected to the video processor 20 with the cable 51, the read-out section 23 in the video processor 20 reads out the endoscope-specific information stored in the identification section 15 from the communication section for endoscope 14 through the cable 52 (step S2). The read-out section 23 outputs the read-out endoscope-specific information to the control section 24. The control section 24 performs communication with the control section 35 in the ultrasound observation apparatus 30 through the communication line 54, and transfers the endoscope-specific information read out by the read-out section 23 to the control section 35 (step S3).

On the other hand, in the ultrasound observation apparatus 30, the communication section for observation apparatus 32 tries to establish communication with the communication section for endoscope 14 in the ultrasound endoscope 10, and when the communication is enabled, the communication section for observation apparatus 32 obtains the endoscope-specific information stored in the identification section 15. The read-out section 31 reads out the endoscope-specific information from the communication section for observation apparatus 32, to output the read-out information to the control section 35 (step S11).

The control section 35 cross-checks the endoscope-specific information transmitted from the video processor 20 through the communication line 54 and the endoscope-specific information obtained by the communication section for observation apparatus 32 by wireless communication against each other, to determine whether the transmitted endoscope-specific information and the obtained endoscope-specific information match with each other (step S12). As a result of the cross-check, when determining that the pieces of information match with each other, the control section 35 determines that wireless communication is established between the ultrasound observation apparatus and the ultrasound endoscope 10 connected to the video processor 20 through the wire.

In this case, the control section 35 performs setting required for transmission and reception on the ultrasound endoscope 10 in step S13. That is, the control section 35 causes setting parameters for transmission and reception to be transmitted to the communication section for endoscope 14 through the communication section for observation apparatus 32, to set a state in which the ultrasound image can be transmitted and received between the ultrasound endoscope 10 and the ultrasound observation apparatus. Thus, the ultrasound image is transmitted from the ultrasound endoscope 10 to the ultrasound observation apparatus 30 by wireless communication.

In addition, the control section 35 notifies the control section 24 in the video processor 20 that the ultrasound endoscope 10 has been recognized in the ultrasound observation apparatus 30, through the communication line 54 (step S14). Based on the notification, the video processor 20 recognizes that wireless communication is established between the ultrasound endoscope 10 connected thereto through the wire and the ultrasound observation apparatus 30, and shares information with the ultrasound observation apparatus 30.

When the video processor 20 is brought into a mode for displaying an ultrasound image, the video processor 20 performs image control for displaying the ultrasound image from the ultrasound observation apparatus 30 on the monitor 40. That is, communication is performed between the control sections 24 and 35, and the control section 35 causes the transmission/reception processing section 33 to transmit the ultrasound image obtained from the ultrasound endoscope 10. The image processing section 34 outputs the ultrasound image to the image output section 22 through the communication line 53. The image output section 22 is controlled by the control section 24, to transmit the ultrasound image received through the communication line 53 to the monitor 40 and cause the monitor to display the ultrasound image.

Note that, in this case, the endoscopic image obtained by the image pickup processing section 21 and the ultrasound image from the ultrasound observation apparatus 30 can be transmitted to the monitor 40 and displayed independently or simultaneously on the monitor 40.

In addition, as a result of the cross-check in the step S12 in FIG. 2, when determining that the endoscope-specific information from the video processor 20 and the endoscope-specific information obtained by the communication section for observation apparatus 32 via wireless communication do not match with each other, the control section 35 proceeds the processing to step S15. In this case, the control section 35 does not transmit the information necessary for transmission and reception to the ultrasound endoscope 10. In addition, the control section 35 outputs a notification indicating that the ultrasound endoscope, which is a wireless communication partner, is a non-compliant device to the control section 24 in the video processor 20. In this case, the control section 24 causes the monitor 40 to display an indication showing that the ultrasound endoscope 10 connected to the video processor 20 through the wire and the endoscope 10 which establishes a communication with the ultrasound observation apparatus 30 are different ultrasound endoscopes, to notify the operator that communication is not established between the ultrasound endoscope 10 and the ultrasound observation apparatus 30.

Thus, in the present embodiment, cross-check of the pieces of obtained endoscope-specific information is performed between the video processor connected to the ultrasound endoscope through the wire and the ultrasound observation apparatus connected to the ultrasound endoscope via wireless communication, to confirm whether the ultrasound endoscope connected to the video processor through the wire is the same as the ultrasound endoscope connected to the ultrasound observation apparatus via wireless communication. That is, even in the case where the method of establishing communication wirelessly between the ultrasound observation apparatus and the ultrasound endoscope is employed, the ultrasound observation apparatus connected to the video processor can be surely connected to the ultrasound endoscope via wireless communication. That is, the ultrasound endoscope and the ultrasound observation apparatus can be easily connected to each other, which enables a system performance for enabling switching between the endoscopic image and the ultrasound image to be ensured. In addition, confirmation of the communication establishment enables information sharing between the video processor and the ultrasound observation apparatus. As a result, the endoscopic image and the ultrasound image for the same one patient can be displayed and recorded while unifying the management of these images.

In addition, in FIG. 2, the processing in the step S13 and the processing in the step S14 are performed sequentially. However, these processings may be performed simultaneously.

Furthermore, in FIG. 2, the endoscope-specific information is transferred to the ultrasound observation apparatus 30 to determine the matching of the pieces of endoscope-specific information in the ultrasound observation apparatus 30. However, without the transmission of the endoscope-specific information to the ultrasound observation apparatus 30, when the video processor 20 reads out the endoscope-specific information, the ultrasound observation apparatus 30 may read out the endoscope-specific information to transfer the read-out endoscope-specific information to the video processor 20, and the video processor 20 may determine the matching of the pieces of read-out endoscope-specific information, and display an image indicating the result of the matching on the monitor.

Second Embodiment

Figure 3:
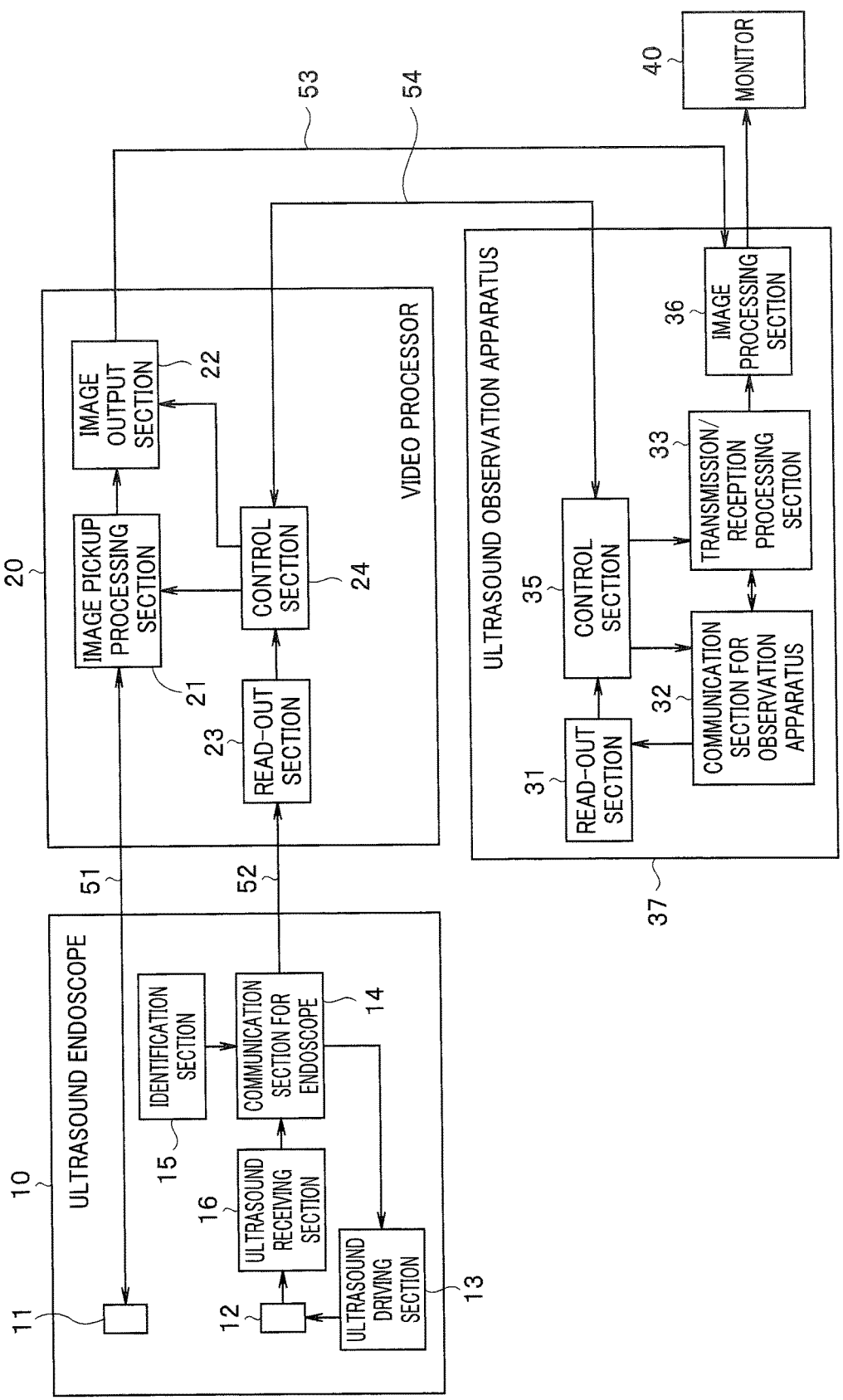
FIG. 3 is a block diagram showing a second embodiment of the present invention.

FIG. 3 is a block diagram showing the second embodiment of the present invention. In FIG. 3, the constituent elements same as those in FIG. 1 are attached with the same reference signs and descriptions thereof will be omitted. In the present embodiment, output to the monitor 40 is performed by an ultrasound observation apparatus 37.

The ultrasound observation apparatus 37 in the present embodiment is different from the ultrasound observation apparatus 30 in FIG. 1 in that an image processing section 36 is used instead of the image processing section 34. In the present embodiment, the image output section 22 of the video processor 20 outputs an endoscopic image to the image processing section 36 of the ultrasound observation apparatus 37 through the communication line 53.

The image processing section 36 performs predetermined image signal processing on the ultrasound image received from the ultrasound endoscope 10 by the communication section for observation apparatus 32, to output the processed ultrasound image to the monitor 40, and is capable of outputting the endoscopic image, which has been inputted from the image output section 22 through the communication line 53, to the monitor 40. In addition, the image processing section 36 is also capable of combining the endoscopic image and the ultrasound image, to output the combined image to the monitor 40. The control section 35 communicates with the control section 24 to control the output of the endoscopic image and the ultrasound image to the monitor 40.

Also in the present embodiment thus configured, the process for performing communication between the video processor 20 connected to the ultrasound endoscope 10 through the wire and the ultrasound observation apparatus 37, to cross-check the pieces of endoscope-specific information, and establishing connection via wireless communication between the ultrasound endoscope 10 and the ultrasound observation apparatus 37 is the same as that in the first embodiment.

In the present embodiment, the control section 35 in the ultrasound observation apparatus 37 performs the control for outputting the endoscopic image and the ultrasound image obtained by operating the ultrasound endoscope 10 to the monitor 40. The control section 35 causes the endoscopic image transmitted from the video processor 20 and the ultrasound image obtained from the ultrasound endoscope 10 by the communication section for observation apparatus 32 via wireless communication to be displayed on the monitor 40 by switching these images or to be displayed on the monitor simultaneously.

Other working and effects are the same as those in the first embodiment.

Third Embodiment

Figure 4:
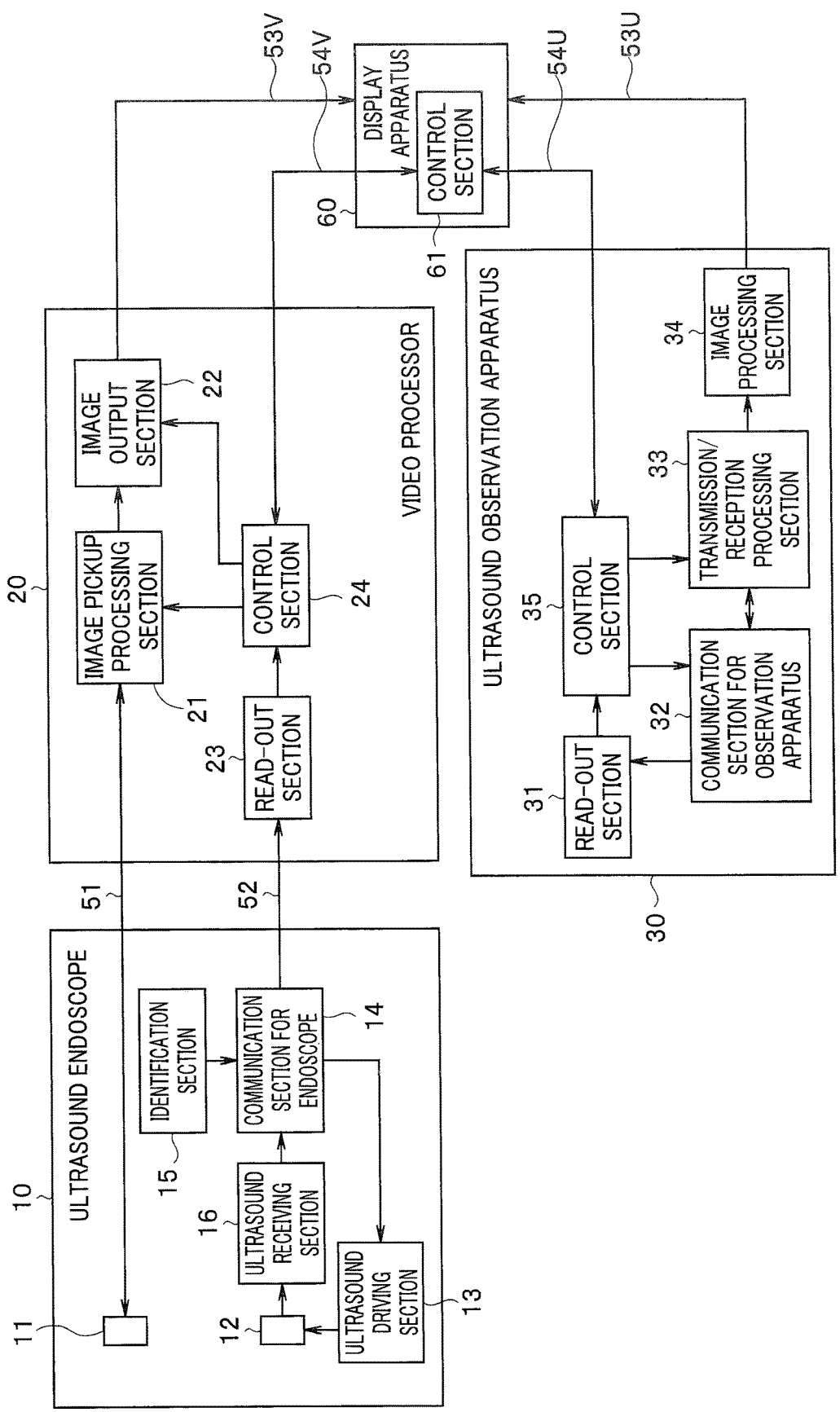
FIG. 4 is a block diagram showing a third embodiment of the present invention.

FIG. 4 is a block diagram showing the third embodiment of the present invention. In FIG. 4, the constituent elements same as those in FIG. 1 are attached with the same reference signs and descriptions thereof will be omitted. An ultrasound endoscope system according to the present embodiment employs a display apparatus 60 including a control section 61, instead of the monitor 40. In the first and second embodiments, the control section 24 in the video processor 20 and the control section 35 in the ultrasound observation apparatus 30 are configured to determine the establishment of the communication with the ultrasound endoscope 10. In contrast, in the present embodiment, a control section provided in another part of the ultrasound endoscope system is configured to determine the establishment of the communication with the ultrasound endoscope 10. FIG. 4 shows an example in which the control section 61 provided in the display apparatus 60 determines the establishment of the communication.

The control section 24 communicates with the control section 61 in the display apparatus 60 via a communication line 54V, and the control section 35 communicates with the control section 61 in the display apparatus 60 via a communication line 54U. In addition, the image output section 22 supplies an endoscopic image to the display apparatus 60 through a communication line 53V and the image processing section 34 supplies an ultrasound image to the display apparatus 60 through a communication line 53U.

The endoscopic image and the ultrasound image are inputted to the display apparatus 60. The display apparatus 60 is controlled by the control section 61 and configured to be able to selectively or simultaneously display these inputted images on a display screen, not shown.

The control section 61 in the display apparatus 60 receives the endoscope-specific information, which has been read out by the read-out section 23, from the control section 24, and receives the endoscope-specific information, which has been read out by the read-out section 31, from the control section 35. The control section 61 cross-checks these pieces of endoscope-specific information against each other, to determine whether or not the wire connection and the wireless connection are normally established, that is, determines whether or not the communication is established wirelessly between the ultrasound endoscope 10 connected to the video processor 20 through the wire and the ultrasound observation apparatus 30.

When determining that the wireless communication has been established between the ultrasound endoscope 10 connected to the video processor 20 through the wire and the ultrasound observation apparatus 30, the control section 61 causes the control sections 24 and 35 to share information. Furthermore, the display mode is specified by the control sections 24 and 35, and the control section 61 causes the endoscopic image and the ultrasound image to be displayed selectively or simultaneously on the display screen in the specified display mode.

Figure 5:
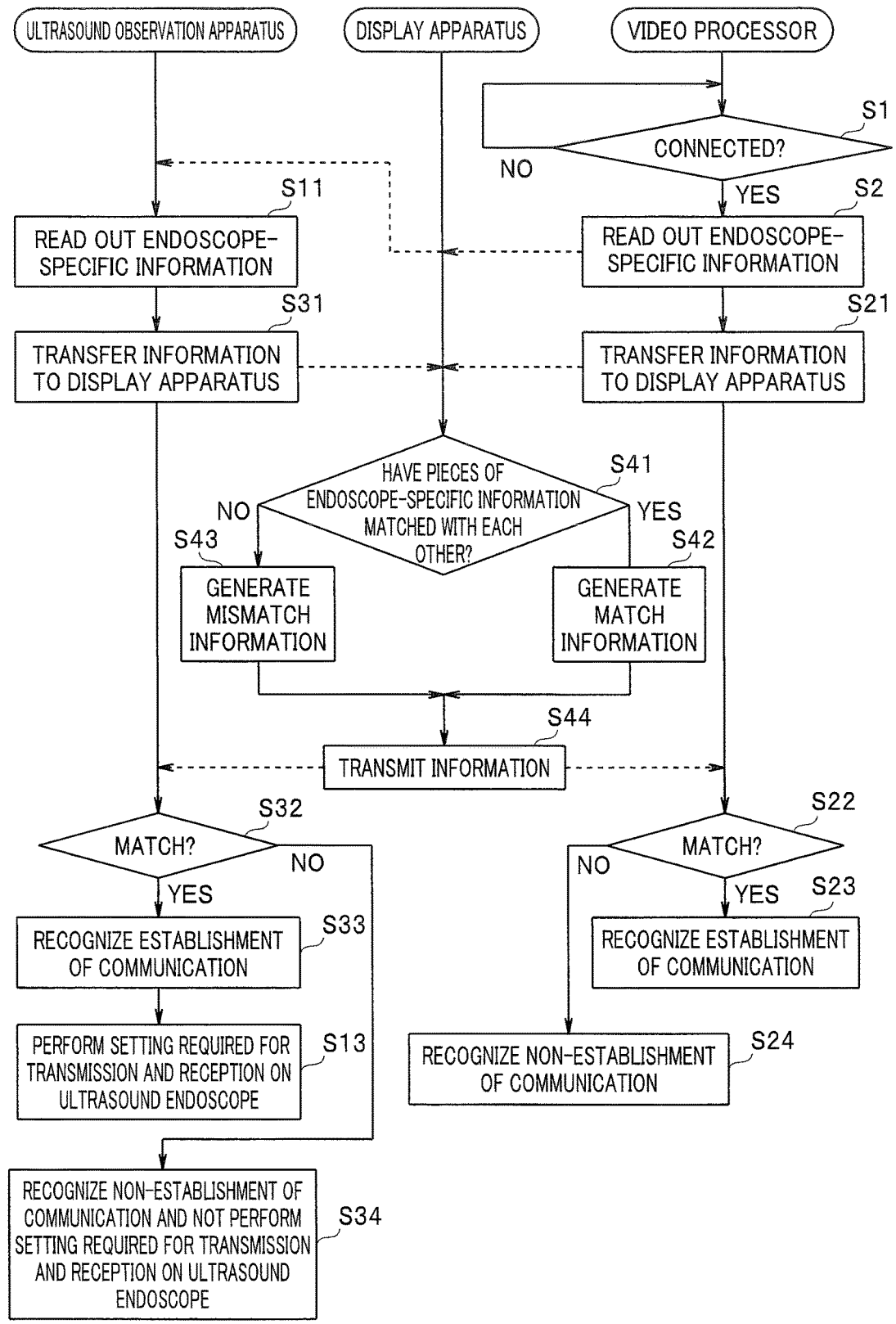
FIG. 5 is a flowchart for describing an operation in the third embodiment.

Next, the operation in the present embodiment thus configured will be described with reference to the flowchart in FIG. 5. In FIG. 5, the same processing steps as those in FIG. 2 are attached with the same reference signs and descriptions thereof will be omitted. In FIG. 5, the operation of the ultrasound observation apparatus 30 is shown on the left side, the operation of the display apparatus 60 is shown in the center, and the operation of the video processor 20 is shown on the right side, and each of the dashed-line arrows shows communication.

When the video processor 20 reads out the endoscopic-specific information stored in the identification section 15 from the communication section for endoscope 14, through the cable 52 (step S2), the control section 24 notifies the control section 35 in the ultrasound observation apparatus 30 that the endoscope-specific information has been read out, through the display apparatus 60. In response to the notification, the ultrasound observation apparatus 30 communicates with the ultrasound endoscope 10 through the communication section for observation apparatus 32, to obtain the endoscope-specific information. The read-out section 31 reads out the endoscope-specific information from the communication section for observation apparatus 32 (step S31), and outputs the read-out information to the control section 35.

In the present embodiment, the control section 24 in the video processor 20 transfers the endoscope-specific information obtained by the read-out section 23 to the display apparatus 60 through the communication line 54V (step S21), and the control section 35 in the ultrasound observation apparatus 30 transfers the endoscope-specific information read out by the read-out section 31 to the display apparatus 60 through the communication line 54U (step S31).

The control section 61 of the display apparatus 60 cross-checks the endoscope-specific information transferred from the video processor 20 and the endoscope-specific information transferred from the ultrasound observation apparatus 30 against each other, to determine match or mismatch of the pieces of endoscope-specific information (step S41). Furthermore, when determining that the pieces of endoscope-specific information match with each other, the control section 61 generates information indicating the match (match information) in step S42 (step S42). When determining that the pieces of endoscope-specific information do not match with each other, the control section 61 generates information indicating the mismatch (mismatch information) in step S43 (step S43). The control section 61 outputs the match information or the mismatch information to the control sections 24 and 35 through the communication lines 54V and 54U (step S44).

The control section 24 in the video processor 20 determines whether the received information is the match information or the mismatch information (step S22). When determining that the received information is the match information, the control section 24 recognizes that communication has been established between the ultrasound endoscope 10 connected to the video processor 20 through the wire and the ultrasound observation apparatus 30 (step S23). Furthermore, when determining that the received information is the mismatch information, the control section 24 recognizes that communication is not established between the ultrasound endoscope 10 connected to the video processor 20 through the wire and the ultrasound observation apparatus 30 (step S24).

The control section 35 in the ultrasound observation apparatus 30 determines whether the received information is the match information or the mismatch information in step S32. When determining that the received information is the match information, the control section 35 recognizes that wireless communication has been established between the ultrasound endoscope 10 connected to the video processor 20 through the wire and the communication section for observation apparatus 32 (step S33). In this case, the control section 35 performs setting required for transmission and reception on the ultrasound endoscope in step S13.

Furthermore, when determining that the received information is the mismatch information, the control section 35 recognizes that wireless communication is not established between the ultrasound endoscope 10 connected to the video processor 20 through the wire and the communication section for observation apparatus 32, the control section 35 does not transmit the information required for transmission and reception to the ultrasound endoscope 10.

When recognizing that communication has been established, the control section 24 in the video processor 20 and the control section 35 in the ultrasound observation apparatus 30 output the endoscopic image and the ultrasound image, respectively, to the display apparatus 60 through the communication lines 53V and 53U. In response to this, the display apparatus 60 displays one of or both of the endoscopic image and the ultrasound image according to the display mode.

When the control section 61 of the display apparatus 60 generates the mismatch information, the control section 61 causes the display screen to display an indication that the ultrasound endoscope as the partner of wireless communication with the ultrasound observation apparatus 30 is a non-compliant device and the ultrasound endoscope 10 connected to the video processor 20 through the wire is different from the ultrasound endoscope 10 which establishes communication with the ultrasound observation apparatus 30. Note that, when the communication has been established, the control section 61 may display an indication of the establishment of communication on the display screen.

Thus, also in the present embodiment, it is possible to obtain the same effects as those in the first embodiment.

Note that, in the above-described embodiments, one video processor 20 and one ultrasound observation apparatus 30 are provided, but a plurality of video processors 20 and a plurality of ultrasound observation apparatuses 30 may be connected to the one display apparatus 60. However, the communication lines and the image communication lines to be connected to the display apparatus 60 have to be a pair for the respective processors and ultrasound observation apparatuses. In the above-described embodiments, description has been made on the example in which the information indicating whether or not the communication is established is displayed on the monitor or the display apparatus. However, a display section made of LCD, LED, or the like may be provided in the ultrasound endoscope system and the information may be displayed on the display section.

The present invention is not limited to the embodiments as they are described above, and can be embodied in the practical stage by modifying constituent elements within a range without departing from the gist of the invention. In addition, various inventions can be formed by appropriately combining the plurality of constituent elements disclosed in the above-described embodiments. For example, some of all constituent elements disclosed in the embodiments may be deleted. Furthermore, constituent elements shown in different embodiments may be appropriately combined.

What is claimed is:

1. An ultrasound endoscope system comprising:
   an ultrasound endoscope comprising:
      an image pickup sensor configured to obtain an optical image of a subject;
      an ultrasound transducer configured to transmit and receive ultrasound to and from the subject; and
      an endoscope-side transmitter configured to transmit:
         an ultrasound signal obtained from the ultrasound received by the ultrasound transducer through wireless transmission; and
         endoscope state information as endoscope-specific information through one or more wires, and through wireless transmission;
   a video processor configured to:
      perform image signal processing on an endoscopic image based on the optical image obtained by the image pickup sensor, the endoscopic image being fed from the ultrasound endoscope to the video processor through the one or more wires; and
      read out the endoscope state information of the ultrasound endoscope, the endoscope state information being fed from the ultrasound endoscope to the video processor through the one or more wires;
   an ultrasound observation apparatus comprising:
      an ultrasound observation apparatus-side receiver configured to wirelessly receive the ultrasound signal and the endoscope state information; and
      an ultrasound observation apparatus-side processor configured to:
         generate an ultrasound image based on the ultrasound signal wirelessly received by the ultrasound observation apparatus-side receiver; and
         read out the endoscope state information wirelessly received by the ultrasound observation apparatus-side receiver; and
      a controller configured to:
         determine whether the endoscope state information fed from the ultrasound endoscope through the one or more wires and read out by the video processor matches the endoscope state information wirelessly received by the ultrasound observation apparatus-side receiver and read out by the ultrasound observation apparatus-side processor; and
         cause sharing of information related to the subject to be started between the video processor and the ultrasound observation apparatus in response to a determination that the endoscope state information read out by the video processor matches the endoscope state information read out by the ultrasound observation apparatus-side processor.

2. The ultrasound endoscope system according to claim 1, wherein the endoscope state information comprises identification information of the ultrasound endoscope.

3. The ultrasound endoscope system according to claim 1, wherein the video processor is connected to the ultrasound observation apparatus-side processor by an image communication line, and
   wherein one of the video processor and the ultrasound observation apparatus-side processor is configured to:
      obtain image information through the image communication line from the other of the video processor and the ultrasound observation apparatus-side processor, and
      control a display to display both of an image based on the endoscopic image and an image based on the ultrasound image to be displayed in a switchable manner.

4. The ultrasound endoscope system according to claim 1, further comprising,
   a display apparatus comprising:
      a display; and
      the controller, wherein the controller is configured to, in response to the determination that the endoscope state information read out by the video processor matches the endoscope state information read out by the ultrasound observation apparatus-side processor, control the display to switchably display an image based on the endoscopic image and an image based on the ultrasound image.

5. The ultrasound endoscope system according to claim 3, wherein the one of the video processor and the ultrasound observation apparatus-side processor is configured to, in response to the determination that the endoscope state information read out by the video processor matches the endoscope state information read out by the ultrasound observation apparatus-side processor, control the display to display a state of wireless connection between:
the ultrasound endoscope connected with the video processor through the one or more wires; and
the ultrasound observation apparatus.

6. The ultrasound endoscope system according to claim 1, wherein the ultrasound endoscope comprises:
a display configured to display a state of wireless connection between:
the ultrasound endoscope connected with the video processor through the one or more wires; and
the ultrasound apparatus, in response to the determination that the endoscope state information read out by the video processor matches the endoscope state information read out by the ultrasound observation apparatus-side processor.

7. A communication method of an ultrasound endoscope system, the ultrasound endoscope system comprising:
an ultrasound endoscope comprising:
an image pickup sensor configured to obtain an optical image of a subject;
an ultrasound transducer configured to transmit and receive ultrasound to and from the subject; and
an endoscope-side transmitter configured to transmit:
an ultrasound signal obtained from the ultrasound received by the ultrasound transducer through wireless transmission; and
endoscope state information as endoscope-specific information through one or more wires, and through wireless transmission;
a video processor configured to:
perform image signal processing on an endoscopic image based on the optical image obtained by the image pickup sensor, the endoscopic image being fed from the ultrasound endoscope to the video processor through the one or more wires; and
read out the endoscope state information of the ultrasound endoscope, the endoscope state information being fed from the ultrasound endoscope to the video processor through the one or more wires; and
an ultrasound observation apparatus comprising:
an ultrasound observation apparatus-side receiver configured to wirelessly receive the ultrasound signal and the endoscope state information; and
an ultrasound observation apparatus-side processor configured to:
generate an ultrasound image based on the ultrasound signal wirelessly received by the ultrasound observation apparatus-side receiver; and
read out the endoscope state information wirelessly received by the ultrasound observation apparatus-side receiver,
wherein the communication method comprises:
determining whether the endoscope state information fed from the ultrasound endoscope through the one or more wires and read out by the video processor matches the endoscope state information wirelessly received by the ultrasound observation apparatus-side receiver and read out by the ultrasound observation apparatus-side processor; and
causing sharing of information related to the subject to be started between the video processor and the ultrasound observation apparatus in response to a determination that the endoscope state information read out by the video processor matches the endoscope state information read out by the ultrasound observation apparatus-side processor.

\* \* \* \* \*